(12) United States Patent
Smith

(10) Patent No.: US 8,152,798 B2
(45) Date of Patent: Apr. 10, 2012

(54) SURGICAL VARIABLE-ANGLE ILLUMINATOR

(75) Inventor: Ronald T. Smith, Newport Coast, CA (US)

(73) Assignee: Novartis AG, Basel (CH)

(*) Notice: Subject to any disclaimer, the term of this patent is extended or adjusted under 35 U.S.C. 154(b) by 1199 days.

(21) Appl. No.: 11/590,011

(22) Filed: Oct. 31, 2006

(65) Prior Publication Data
US 2007/0100326 A1  May 3, 2007

Related U.S. Application Data

(60) Provisional application No. 60/731,942, filed on Oct. 31, 2005.

(51) Int. Cl.
*A61B 18/18* (2006.01)
(52) U.S. Cl. .............. 606/16; 606/4; 128/898; 385/100; 362/558; 362/572
(58) Field of Classification Search .............. 606/2–19; 607/88–95
See application file for complete search history.

(56) References Cited

U.S. PATENT DOCUMENTS

| | | | |
|---|---|---|---|
| 4,222,375 A | 9/1980 | Martinez | |
| 4,654,532 A | 3/1987 | Hirschfeld | |
| 4,898,450 A * | 2/1990 | Jannson et al. | 385/50 |
| 5,196,005 A * | 3/1993 | Doiron et al. | 606/7 |
| 5,430,620 A * | 7/1995 | Li et al. | 362/572 |
| 5,514,125 A | 5/1996 | Lasser | |
| 5,615,673 A * | 4/1997 | Berger et al. | 600/326 |
| 5,624,438 A | 4/1997 | Turner | |
| 5,729,643 A | 3/1998 | Hmelar et al. | |
| 5,782,825 A | 7/1998 | Anderson | |
| 5,784,508 A | 7/1998 | Turner | |
| 5,888,194 A | 3/1999 | Utusmi et al. | |
| 5,997,155 A * | 12/1999 | Ducharme et al. | 362/298 |

(Continued)

FOREIGN PATENT DOCUMENTS

DE  3630351  3/1987
(Continued)

OTHER PUBLICATIONS

Notification of Transmittal of the International Search Report and The Written Opinion of the International Searching Authority, or the Declaration.

(Continued)

*Primary Examiner* — Henry M Johnson, III
*Assistant Examiner* — Aisha Hunte
(74) *Attorney, Agent, or Firm* — Darien Reddick

(57) ABSTRACT

A variable-angle, wide-angle illuminator is disclosed, one embodiment being a small-gauge, variable-angle illumination surgical system comprising: a light source for providing a light beam; an optical cable, optically coupled to the light source for receiving and transmitting the light beam; a handpiece, operably coupled to the optical cable; an optical fiber, operably coupled to the handpiece, wherein the optical fiber is optically coupled to the optical cable to receive and transmit the light beam; an optical assembly, optically coupled to a distal end of the optical fiber, for receiving the light beam and providing the light beam to illuminate a surgical field; and a cannula, operably coupled to the handpiece and optical assembly, for housing and directing the optical assembly to illuminate selected area. The optical assembly can comprise a fiber/polymer-dispersed-liquid-crystal ("PDLC") diffuser optically coupled to an optical needle or a nested compound parabolic concentrator ("CPC") cone.

7 Claims, 6 Drawing Sheets

U.S. PATENT DOCUMENTS

| | | | |
|---|---|---|---|
| 6,094,517 | A | 7/2000 | Yuuki |
| 6,254,530 | B1 | 7/2001 | Ryan, Jr. |
| 6,428,553 | B1 | 8/2002 | Trese |
| 2003/0169603 | A1 | 9/2003 | Luloh et al. |
| 2005/0075628 | A1* | 4/2005 | Cazzini et al. ............... 606/4 |
| 2005/0078910 | A1* | 4/2005 | Hickingbotham .............. 385/31 |
| 2006/0018596 | A1 | 1/2006 | Loebel |

FOREIGN PATENT DOCUMENTS

| | | |
|---|---|---|
| DE | 10051057 | 5/2002 |
| EP | 1522290 | 4/2005 |
| EP | 1522290 A1 | 4/2005 |
| RU | 2209054 | 7/2003 |
| WO | WO 97/22304 | 6/1997 |
| WO | WO 2004/006749 | 1/2004 |
| WO | WO 2005/070490 | 8/2005 |

OTHER PUBLICATIONS

PCT International Preliminary Report on Patentability, PCT/US2006/042398, Oct. 31, 2006, 8 pages.

International Search and Report and Written Opinion of the International Searching Authority for PCT/US2006/042398, filed Oct. 31, 2006; Publication No. WO2007/053591, Published May 10, 2007; 14 pages, Mailing Date Jul. 9, 2007.

* cited by examiner

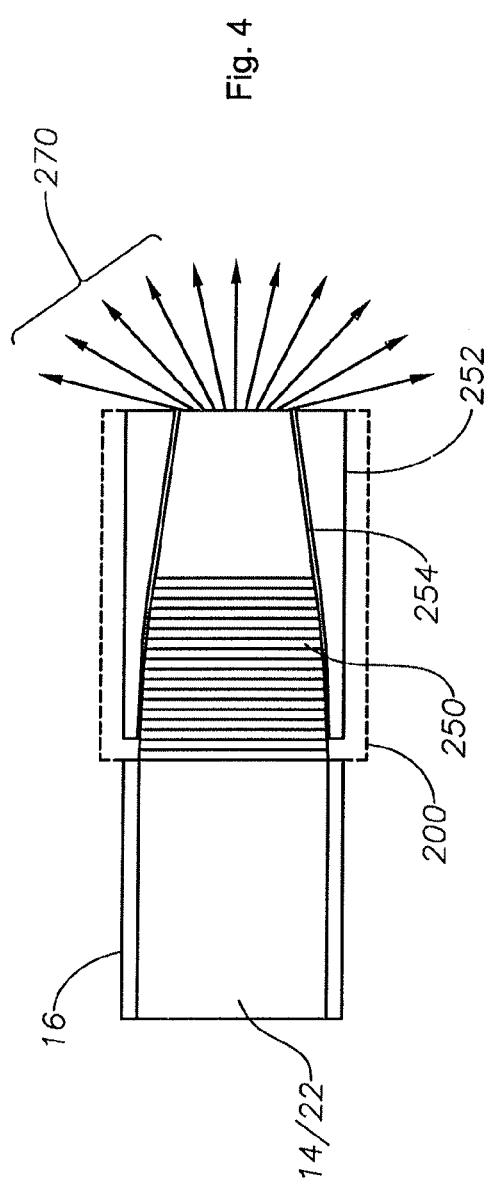
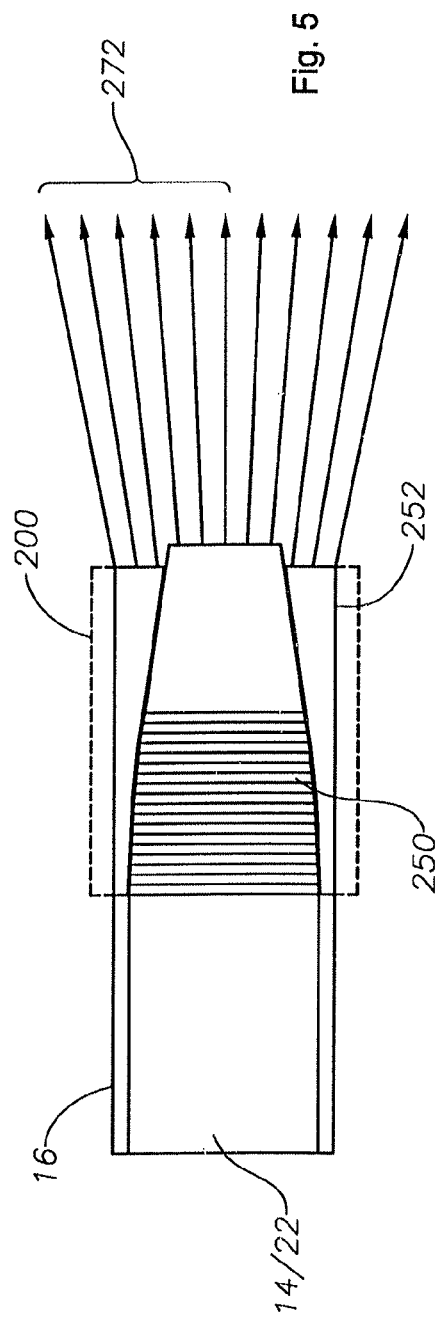

SURGICAL VARIABLE-ANGLE ILLUMINATOR

CROSS-REFERENCE TO RELATED APPLICATIONS

This application claims priority under 35 U.S.C. §119 to U.S. Provisional Patent Application No. 60/731,942, filed Oct. 31, 2005, the entire contents of which are incorporated herein by reference.

TECHNICAL FIELD OF THE INVENTION

The present invention relates generally to surgical instrumentation. In particular, the present invention relates to surgical instruments for illuminating an area during eye surgery. Even more particularly, the present invention relates to a variable-angle, small gauge, wide-angle illuminator for illumination of a surgical field.

BACKGROUND OF THE INVENTION

In ophthalmic surgery, and in particular in vitreo-retinal surgery, it is desirable to use a wide-angle surgical microscope system to view as large a portion of the retina as possible. Wide-angle objective lenses for such microscopic systems exist, but they require a wider illumination field than that provided by the cone of illumination of a typical fiber-optic probe. As a result, various technologies have been developed to increase the beam spreading of the relatively incoherent light provided by a fiber-optic illuminator. These known wide-angle illuminators can thus illuminate a larger portion of the retina as required by current wide-angle surgical microscope systems. Currently existing wide-angle illuminators, however, display several disadvantages.

One disadvantage exhibited by some prior art wide-angle illuminators for ophthalmic surgery is matching of the light refracting index of the vitreous eye fluid to that of the light refracting surface of the lens of the illuminator that comes in contact with the vitreous eye fluid. Contact of the vitreous eye fluid with the light refracting surface of the light spreading lens of such prior art systems results in sub-optimal light refraction due to index switching caused by the vitreous eye fluid. U.S. Pat. No. 5,624,438, entitled "Retinal Wide-Angle Illuminator For Eye Surgery," and issued to R. Scott Turner, provides a system for overcoming the effect of refractive index matching through the use of a high refractive-index step, mediated by the presence of an air-gap. The air-gap is presented between the distal end of an optical fiber and the light refracting surface of the illuminator lens. The light emanating from the optical wave guide (i.e., the optical fiber) will therefore undergo angular dispersion without any index switching that might be caused by contact with the vitreous eye fluid before it passes through the light refracting surface of the illuminator lens.

Another disadvantage of currently available wide-angle illuminators is glare. Glare results when the source of the illumination is small and bright, and the user (e.g., an ophthalmic surgeon) has a direct line of sight to the small bright illumination source. Glare is unwanted stray radiation that provides no useful illumination, and either distracts an observer or obscures an object under observation. Glare can be corrected for in current wide-angle illuminators, but typically only by reducing the total illumination light flux, which reduces the amount of light available for observation by the surgeon. For example, the "bullet probe" manufactured by Alcon Laboratories, Inc., of Fort Worth, Tex., achieves wide-angle illumination by using a bullet-shaped fiber having a surface diffusive finish to scatter light emanating from the distal end of an optical fiber. To reduce glare, the bullet probe can use a geometric shield, which reduces the illumination angle by reducing the overall available light flux.

A further disadvantage of prior art wide-angle illuminators is that they do not provide for varying the illumination angle (angular spread) of the light source to adjust illumination for different conditions within the surgical field in real time.

Therefore, a need exists for a variable-angle, wide-angle illuminator that can reduce or eliminate the problems of associated with prior art wide-angle illuminators, particularly the problem of varying the angular spread of the emitted light in real time.

BRIEF SUMMARY OF THE INVENTION

The embodiments of the variable-angle, wide-angle surgical illuminator of the present invention substantially meet these needs and others. One embodiment of this invention is a small-gauge, variable-angle illumination surgical system comprising: a light source for providing a light beam; an optical cable, optically coupled to the light source for receiving and transmitting the light beam; a handpiece, operably coupled to the optical cable; an optical fiber, operably coupled to the handpiece, wherein the optical fiber is optically coupled to the optical cable to receive and transmit the light beam; an optical assembly, optically coupled to a distal end of the optical fiber, for receiving the light beam and providing the light beam to illuminate an area; and a cannula, operably coupled to the handpiece and optical assembly, for housing and directing the optical assembly.

The optical assembly can comprise a fiber/polymer-dispersed-liquid-crystal ("PDLC") diffuser/glass needle or a nested compound parabolic concentrator ("CPC") cone. In the PDLC diffuser/glass needle embodiment, the fiber can be a standard endo-illuminator optical fiber with 0.50 NA or similar value. The light beam from the light source is transmitted by the optical fiber and provided to a PDLC diffuser for further transmission and diffusion of the light beam. The degree of diffusion of the light beam at the PDLC diffuser can be electrically controlled and can be varied from no diffusion to a very high degree of diffusion. After passing through the PDLC diffuser, the light beam is provided to an optical needle or fiber (e.g., glass) that transmits the light beam to illuminate a desired area, such as a surgical site in the eye.

In the CPC cone embodiment, the distal end of the optical fiber is terminated in a CPC-cone shape that angularly spreads the light out to a high off-axis angle and emits the light out of the distal end of the cannula with high efficiency. Almost all of the light beam escapes the optical fiber and CPC-cone through the planar distal end face. A male CPC-cone is separated from a truncated female CPC-cone by a small air gap. When the male and female CPC-cones are pulled together to make optical contact, the light from the male CPC-cone element is freely transmitted into the female CPC-cone element, and the resultant light is emitted over a greatly reduced angular spread.

The cannula, optical assembly and the handpiece can be fabricated from biocompatible materials. The optical cable can comprise a first optical connector operably coupled to the light source and a second optical connector operably coupled to the handpiece (to optically couple the optical cable to the optical fiber housed within the handpiece and cannula). These connectors can be SMA optical fiber connectors. The optical assembly, optical fiber and optical cable (i.e., the optical fibers within the optical cable) can be of a compatible gauge so as to transmit the light beam from the light source to the surgical field. For example, all three elements could be of equal gauge.

Other embodiments of the present invention can include a method for wide-angle illumination of a surgical field using a variable-angle illuminator in accordance with the teachings of this invention, and a surgical handpiece embodiment of the variable-angle illuminator of the present invention for use in ophthalmic surgery. Further, embodiments of this invention can be incorporated within a surgical machine or system for use in ophthalmic or other surgery. Other uses for a variable-angle, wide-angle illuminator designed in accordance with the teachings of this invention will be known to those having skill the art.

BRIEF DESCRIPTION OF THE SEVERAL VIEWS OF THE DRAWINGS

A more complete understanding of the present invention and the advantages thereof may be acquired by referring to the following description, taken in conjunction with the accompanying drawings, in which like reference numbers indicate like features and wherein:

FIGS. 4 and 5 are diagrammatic representations of a nested CPC-cone optical assembly embodiment of the variable-angle illuminator of the present invention;

DETAILED DESCRIPTION OF THE INVENTION

Figure 1:
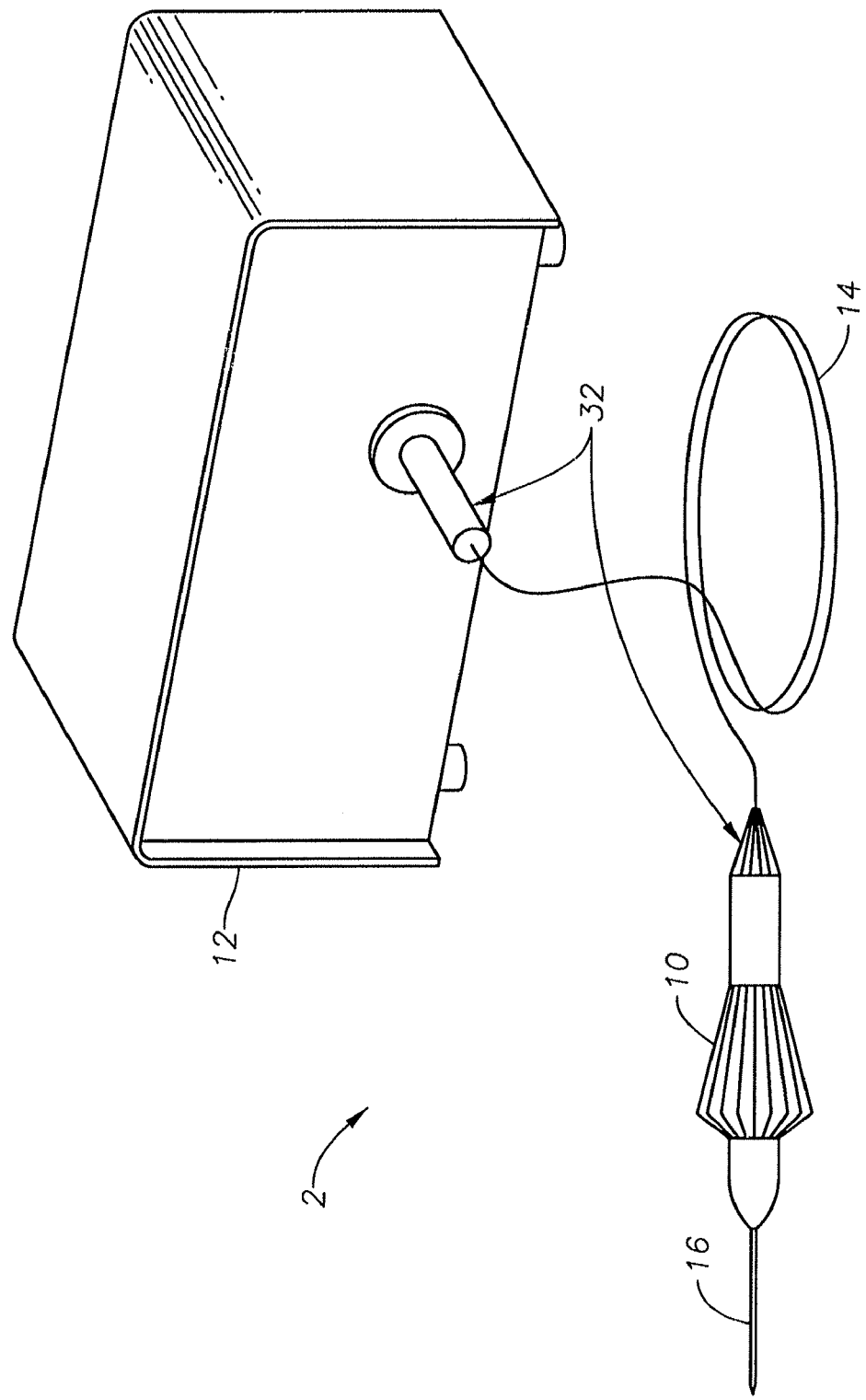
FIG. 1 is a diagrammatic representation of one embodiment of a system for variable, wide-angle illumination in accordance with the teachings of this invention.

Preferred embodiments of the present invention are illustrated in the FIGURES, like numerals being used to refer to like and corresponding parts of the various drawings.

The various embodiments of the present invention provide for a small gauge (e.g., 19, 20, or 25 gauge) optical fiber based endo-illuminator device for use in surgical procedures, such as in vitreo-retinal/posterior segment surgery. Embodiments of this invention can comprise a handpiece, such as the Alcon-Grieshaber Revolution-DSP™ handpiece sold by Alcon Laboratories, Inc., Fort Worth, Tex., connected to a small gauge cannula (e.g., 19, 20, or 25 gauge). The inner dimension of the cannula can be used to house one, or a plurality of, optical fibers and/or a diffusive optical element in accordance with the teachings of this invention. Embodiments of the wide-angle illuminator can be configured for use in the general field of ophthalmic surgery. However, it is contemplated and it will be realized by those skilled in the art that the scope of the present invention is not limited to ophthalmology, but may be applied generally to other areas of surgery where wide-angle and/or variable angle illumination may be required.

An embodiment of the variable-angle, wide-angle illuminator of this invention can comprise a light diffusive optical assembly, a stem, and a handpiece fabricated from biocompatible polymeric materials, such that the invasive portion of the wide-angle illuminator is a disposable surgical item. Embodiments of this invention fabricated from biocompatible polymeric materials can be integrated into a low cost, articulated handpiece mechanism, such that these embodiments can comprise an inexpensive disposable illuminator instrument.

The PDLC diffuser embodiments of the present invention rely on the principle that liquid crystal molecules are rotated by the presence of an electric field. With no electric field, the liquid crystal molecules are randomly oriented and the PDLC layer is highly diffusing. As an electric field is applied and strengthened, the liquid crystal molecules become increasingly lined up parallel to the electric field. With a sufficient electric field strength, the liquid crystal molecules are lined up and the PDLC layer is essentially non-diffusive.

The nested CPC-cone embodiments of the present invention rely on the principle that light within a CPC-cone is confined by total internal reflection of rays off of the surface/air interface. Thus, as long as the male CPC-cone of various embodiments of this invention is surrounded by air, the light transmitted within the CPC-cone will be confined within the male CPC-cone and will funnel down to the end of the CPC-cone where it will be emitted from the cone distal end with a high angular spread. However, if an air gap between a male and a female CPC-cone is eliminated (e.g., by bringing the male and female CPC-cones into contact), the light transmitted within the male CPC-cone will no longer be confined within the male CPC-cone and subject to its funneling effect. Some of the light will instead pass into the female CPC-cone, and the light emitted from the distal end of the optical assembly will have a greatly reduced angular spread.

FIG. 1 is a diagrammatic representation of a surgical system 2 comprising a handpiece 10 for delivering a beam of light from a light source 12 through cable 14 to a stem (cannula) 16. Cable 14 can be any gauge fiber optic cable as known in the art, but is preferably a cable having 19, 20, or 25 gauge fiber. Further, cable 14 can comprise a single optical fiber or a plurality of optical fibers optically coupled to receive and transmit light from light source 12 to an optical fiber 22 within stem 16 through handpiece 10. Handpiece 10 and Stem 16 are configured to house optical fiber 22 and a diffusive optical assembly, optically coupled to fiber 22 and operable to receive the light from light source 12 and transmit it to illuminate a desired area, such as a surgical site. Embodiments of optical assembly 50 (200) are more clearly illustrated in FIGS. 2-4. Coupling system 32 can comprise an optical fiber connector at each end of cable 14 to optically couple light source 12 to an optical fiber 22/14 within handpiece 10, as discussed more fully below.

Figure 2:
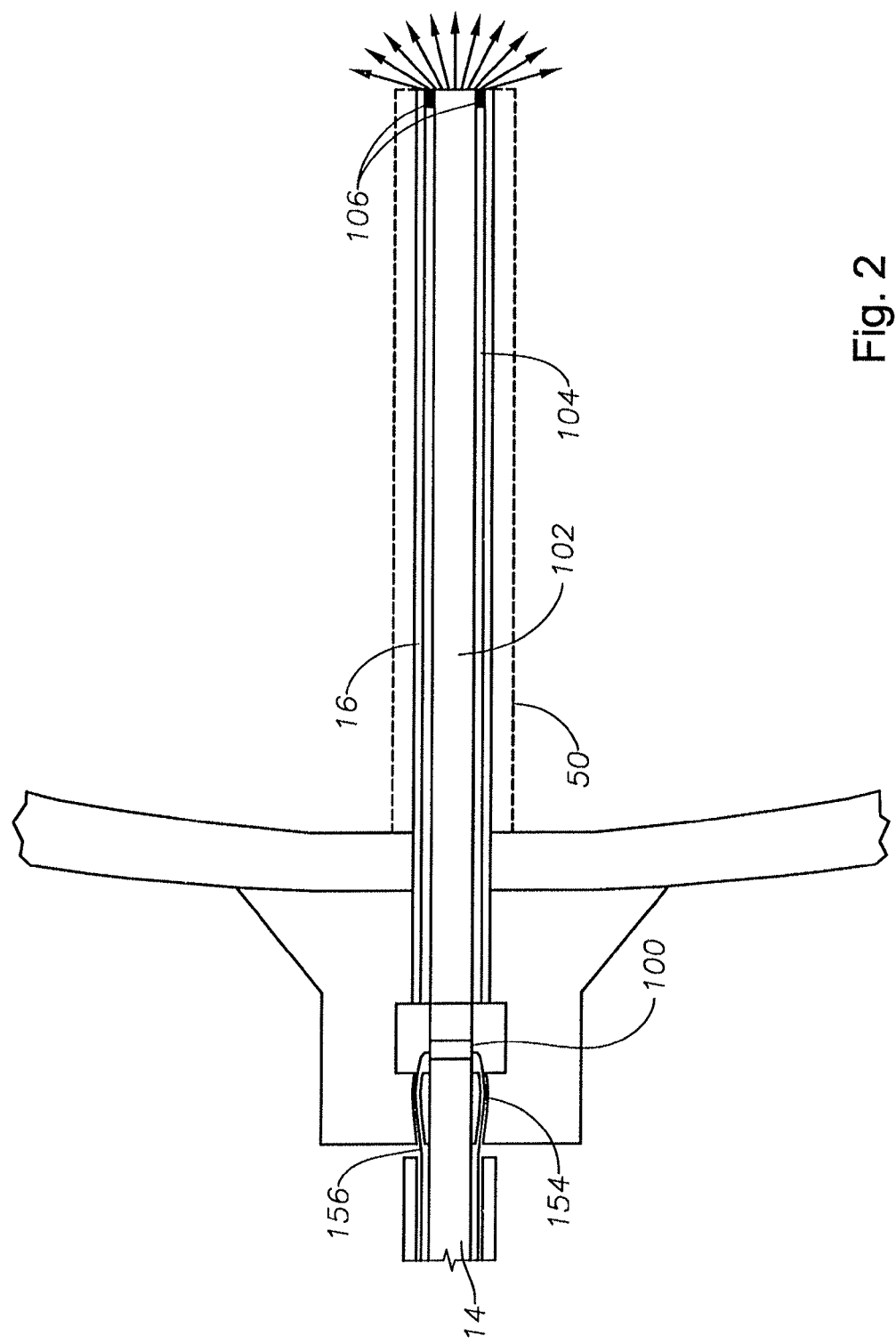
FIG. 2 is a diagrammatic representation of an optical fiber/PDLC diffuser embodiment of the present invention.
Figure 3B:
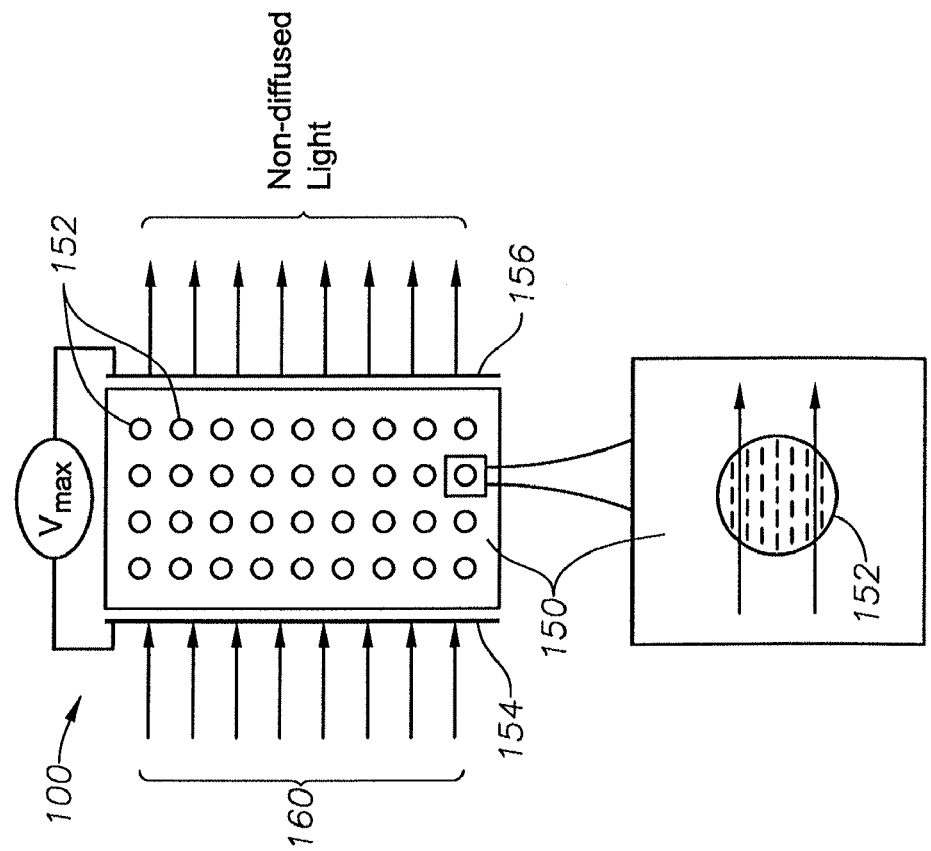
FIGS. 3A and 3B are close-up views of the PDLC diffuser of FIG. 2.
Figure 3A:
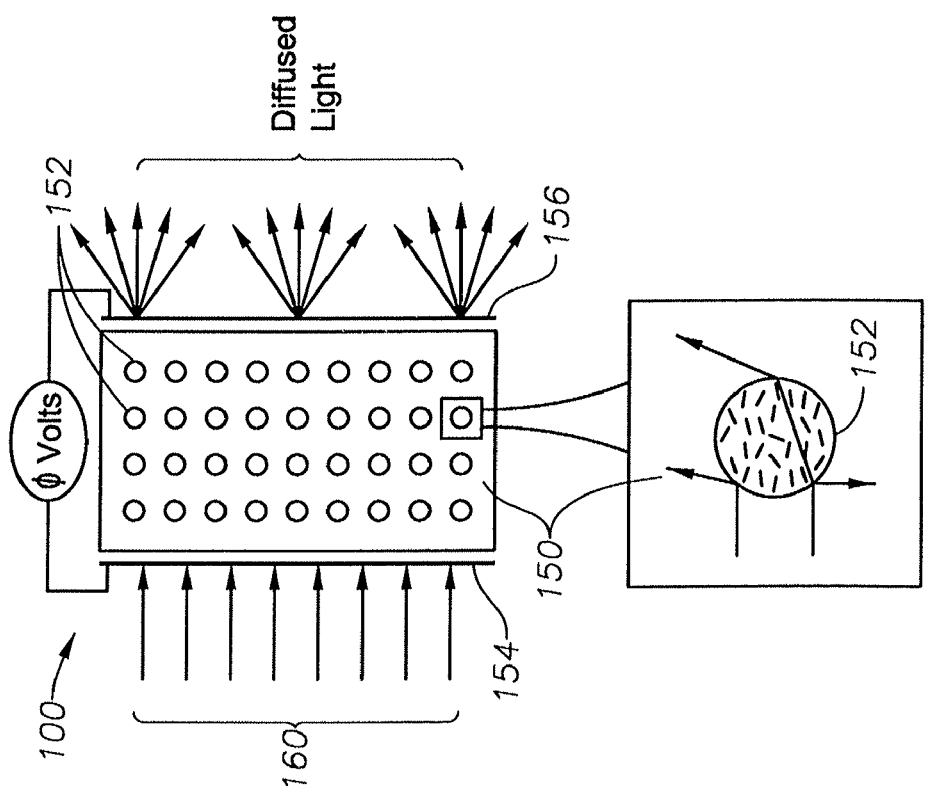

FIG. 2 is a diagrammatic representation of an optical fiber/PDLC diffuser/optical needle embodiment of the present invention. Optical Assembly 50 comprises a PDLC diffuser 100 and an optical needle 102. The PDLC diffuser 100 can consist of a rigid polymer (e.g., plastic) layer 150 into which a plurality of liquid crystal droplets 152 have been dispersed, a transparent (e.g, indium tin oxide) proximal electrode 154 on the entrance (proximal) face of the polymer layer 150, and a transparent distal electrode 156 on the exit (distal) face of the polymer layer 150, as shown in FIGS. 3A and 3B. In the absence of an electric field (FIG. 3A), the liquid crystal molecules within each liquid crystal droplet 152 are randomly oriented. In this state, the effective refractive index of each droplet is significantly different from that of the surrounding rigid polymer. Therefore, there is strong reflection and refraction (as well as scattering) of the incoming light 160 from light source 12 off of the droplet/polymer interface. The aggregate macroscopic effect is significant diffusion of the light 160 passing through the PDLC diffuser 100. However, when a voltage is applied across the PDLC diffuser 100 polymer layer (FIG. 3B), the liquid crystal molecules within each liquid crystal droplet 152 begin to align themselves parallel to the electric field. As they do so, the effective refractive index of the liquid crystal droplets 152 start approaching the refractive index of the surrounding polymer layer 150, and the resultant diffusion of the passing light beam 160 decreases. As the applied voltage increases, the diffusion by the PDLC diffuser 100 decreases. When a threshold voltage is reached, the diffusion of the PDLC diffuser 100 is about zero, and the PDLC diffuser 100 is essentially (about) clear.

The diffuse light emitted from the distal face of the PDLC diffuser 100 is transmitted into cylindrical needle 102 (or an optical fiber 102 with the cladding removed). Needle 102 can be a glass needle/optical fiber. When surrounded by air, the needle 102 has an NA of about 1 and is capable of confining a light beam with a half angle as large as about 90 degrees. Therefore, even at the maximum PDLC diffuser 100 diffusion, essentially all of the diffuse light transmitted to the needle 102 can be transmitted by the needle 102 to its distal end. The needle 102 is enclosed within the stem 16, which can be made of steel. Optical adhesive 106 can be applied at the distal end of the needle 102/cannula 16 assembly to mechanically join the needle 102 to the stem 16, and to ensure the needle 102 is surrounded by air gap 104 within stem 16 by preventing liquid from the eye from getting between the needle 102 and stem 16. To prevent the needle 102 from touching the stem 16 in one or more places, a small number of glass or plastic spacer balls 170 (used routinely in the liquid crystal display industry) can be applied to the needle 102 surface before inserting the needle 102 into the stem 16. The spacer balls 170 will keep the needle 102 separated from stem 16, and the scattered light loss from each spacer ball 170 is anticipated to be negligible.

The electric field applied to the PDLC diffuser 100 can be controlled by any means known to those skilled in the art for controlling the flow of current within an electronic device. For example, a slide mechanism in the handpiece 10 can be used as a rheostat type mechanism (switch), or some other electronic control means can be used, such as a foot controller, that will be familiar to those having skill in the art. The electric field electronic control means can provide a surgeon the ability to continuously vary in real time the angular spread of the light emitted from the illuminator between a narrow field of view (for maximum PDLC diffuser 100 clarity) and a very large field of view (for maximum PDLC diffuser 100 diffusion).

FIGS. 4 and 5 are diagrammatic representations of a nested CPC-cone optical assembly embodiment of the present invention for controlling the angular spread of light emitted from the illuminator. In this embodiment, optical assembly 200 comprises a male CPC-cone element 250 nested within a female CPC-cone element 252, wherein male CPC-cone element 250 and female CPC-cone element 252 are in a moveable relationship to one another. The CPC-cone optical assembly 200 is optically coupled to the distal end of the optical fiber 22/14 and is designed to emit substantially all incoming light out of the planar distal end face 210 of the optical assembly 200 (very little light is emitted out the side surface), emit light over a half angle as large as about 90 degrees, and emit light with very high efficiency. Light passing through the male CPC-cone element 250 remains within the CPC-cone element 250 by total internal reflection at the polymer/air interface on the side wall of the male CPC-cone element 250. The tapering male CPC-cone element 250 causes the light to funnel down and increase its angular spread until the light is emitted from the distal end face 210 over a wide angle.

The wide angular spread of emitted light from the male CPC-cone element 250 depends on air surrounding the CPC-cone element 250 (i.e., on a cone-to-air interface). Therefore, if there is no air gap 254 between the male CPC-cone element 250 and the female CPC-cone element 252, the wide angular spreading of light by the male CPC-cone element 250 cannot occur. One way to eliminate the air gap 254 is illustrated in FIGS. 4 and 5. A male CPC-cone element 250 is nested within a slightly truncated female CPC-cone element 252, with a variable-width air gap 254 between them. In FIG. 4, the female CPC-cone element 252 is in an extended position, causing an air gap 254 to exist between the two CPC-cone elements 250 and 252, and resulting in an angularly broad beam of light 270 emitted from the distal end face 210 of the male CPC-cone element 250. In FIG. 5, the female CPC-cone element 252 is shown in a retracted position in contact with male CPC-cone element 250. The air gap 254 between the CPC-cone elements does not exist when female CPC-cone element 252 is fully retracted. In this case, the two CPC-cone elements 250 and 252 behave optically as if there is no joint between them, and they are effectively a single untapered cylindrical optical element. The resultant beam of emitted light 272 is angularly narrow—about the same angular width as would be emitted from an optical fiber 22/14 without the CPC-cone optical assembly 200.

When the rays of a light beam transmitted by the optical fiber 14/22 and CPC-cone element 250 reflect off of the cone/air interface within the male CPC-cone element 250, an evanescent wave is generated that extends a very short distance (e.g., microns) beyond the CPC-cone surface/air interface and into the surrounding air medium. As long as the surface of the female CPC-cone element 252 remains outside of the evanescent wave region, total internal reflection will occur within the male CPC-cone element 250. If, however, the female CPC-cone element 252 is close enough that its surface is encroaching within the region of the evanescent wave, some of the light ray energy will cross into the female CPC-cone element 252 as a traveling wave. As the air gap 254 between the CPC-cone elements decreases, the amount of light passing into the female CPC-cone element 252 increases. When the air gap 254 is eliminated, essentially 100% of the transmitted light will pass into the female CPC-cone element 252 from the male CPC-cone element 250. Therefore, moving the female CPC-cone element 252 longitudinally only a very short distance along the optical axis will cause the emitted light to switch from a maximum angular spread to a minimum angular spread. In theory it is possible to adjust the air gap 254 to cause an intermediate beam spread somewhere between the two extremes, but in practice this may be extremely difficult to achieve as the sensitivity of the beam spread to the air gap size in the transition region is high.

In one embodiment, the female CPC-cone element 252 can be operably coupled to stem 16 that covers the entire optical fiber 22(14)/CPC-cone optical assembly 200. In such an embodiment, at least two different options can be employed: (1) the stem 16 and female CPC-cone element 252 can be rigidly attached to the handpiece 10 (e.g., to one another) and the optical fiber 22(14)/male CPC-cone element 250 can be operable to move longitudinally along the optical axis, or (2) the optical fiber 22(14) and male CPC-cone element 250 can be rigidly attached to the handpiece 10 and the stem 16 and female CPC-cone element 252 can be operable to move longitudinally along the optical axis. In either case, the switching beam states (longitudinal movement of the moveable components) can be controlled by a slide or toggle switch mechanism in or on the handpiece 10 in a manner that will be known to those having average skill in the art.

When used in an embodiment, optical fiber 22 can be optically coupled to fiber optic cable 14. In some embodiments, however, fiber optic cable 14 can extend through the handpiece 10 and is optically coupled directly to the optical assembly 50 (200) comprising PDLC diffuser 100 or CPC-cone elements 250/252. For these embodiments, a separate optical fiber 22 is not used. When implemented within handpiece 10, optical fiber 22 is of a gauge compatible with the gauge of fiber optic cable 14, such that it can receive and transmit light from fiber optic cable 14. Handpiece 10 can be any surgical handpiece as known in the art, such as the Revolution-DSP™ handpiece sold by Alcon Laboratories, Inc. of Fort Worth, Tex. Light source 12 can be a xenon light source, a halogen light source, or any other light source capable of delivering light through a fiber optic cable. Stem 16 can be a small gauge cannula, preferably on the order of 19, 20, or 25 gauge, as known to those having skill in the art. Stem 16 can be stainless steel or a suitable biocompatible polymer (e.g., PEEK, polyimide, etc.) as known to those having skill in the art.

Figure 7:
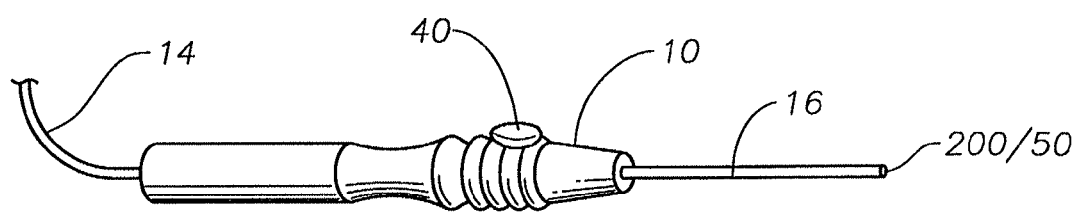
FIG. 7 is a diagram illustrating an embodiment of an adjusting means 40 in accordance with the present invention.

The fiber optic cable 14 or optical fiber 22, CPC-cone elements 250/252 and/or stem 16 (in such combinations as described above) can be operably coupled to the handpiece 10, for example, via an adjusting means 40, as shown in FIG. 7. Adjusting means 40 can comprise, for example, a push/pull mechanism as known to those having skill in the art, such as a piston to which the moveable components are operably coupled. The piston can be controlled via adjusting means 40, which can be a manual mechanical device for moving the piston or an electro-mechanical actuator (switch) for controlling an electro-mechanical means for moving the piston, as will be known to those having skill in the art. Light source 12 can be optically coupled to handpiece 10 (e.g., to fiber 22) using, for example, standard SMA (Scale Manufacturers Association) optical fiber connectors at the ends of fiber optic cable 14. This allows for the efficient coupling of light from the light source 12 through fiber optic cable 14/optical fiber 22 and the handpiece 10 and finally emanating from optical assembly 50 (200) at the distal end of the stem 16. Light source 12 may comprise filters, as known to those skilled in the art, to reduce the damaging thermal effects of absorbed infrared radiation originating at the light source. The light source 12 filter(s) can be used to selectively illuminate a surgical field with different colors of light, such as to excite a surgical dye. Fiber(s) 22 (and/or 14, depending on the embodiment) is/are terminated by optically coupling to the optical assembly 50 (200) comprising PDLC diffuser 100/needle 102 or CPC-cone elements 250/252.

Figure 6:
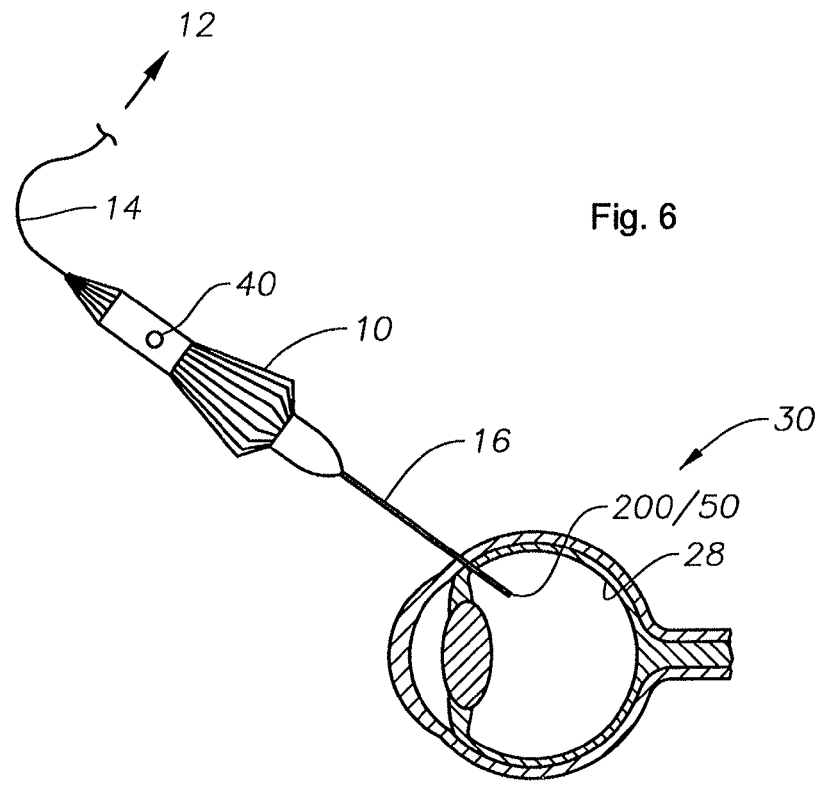
FIG. 6 is a diagram illustrating the use of one embodiment of the variable-angle illuminator of this invention for ophthalmic surgery.

FIG. 6 illustrates the use of one embodiment of the variable-angle, wide-angle illuminator of this invention in an ophthalmic surgery. In operation, handpiece 10 delivers a beam of light through stem 16 (via fiber optic cable 14 and or optical fiber 22) and through optical assembly 50 (200) to illuminate a retina 28 of an eye 30. The collimated light delivered through handpiece 10 to the optical assembly 50 (200) is generated by light source 12 and delivered to illuminate the retina 28 by means of fiber optic cable 14 and coupling system 32. Optical assembly 50 (200) is operable to spread the light beam delivered from light source 12 over as large an area of the retina as, for example, a microscopic wide-angle objective lens permits a surgeon to see.

In one embodiment of the variable-angle, wide-angle illuminator of the present invention, a simple mechanical locking mechanism, as known to those skilled in the art, can permit the illumination angle to be fixed, until released and/or readjusted by the user via the adjusting means 40.

An advantage of the embodiments of the variable-angle, wide-angle illuminator of this invention, is that an operator can vary the angle of illumination of emitted light from the distal end of the illuminator in real time to optimize viewing conditions within the surgical field. The angular spread of the emitted light can thus be controlled as desired by the operator FIG. 7 provides another view of a wide-angle illuminator according to the teachings of this invention showing more clearly an embodiment of adjusting means 40. In this embodiment, adjusting means 40 comprises a slide button, as known to those skilled in the art. Activation of adjusting means 40 on handpiece 10 by, for example, a gentle and reversible sliding action, can cause a change in the diffusion rate of PDLC diffuser 100 or cause a change in the relative positions between male CPC cone element 250 and female CPC cone element 252, in the manner described above. Adjusting means 40 can comprise, for example, a push/pull mechanism as known to those having skill in the art, such as a piston to which the moveable components are operably coupled. The piston can be controlled via adjusting means 40, which can be a manual mechanical device for moving the piston or an electro-mechanical actuator (switch) for controlling an electro-mechanical means for moving the piston, as will be known to those having skill in the art. Adjusting means 40 can also comprise, in other embodiments, a simple on/off switch, as will be known to those having skill in the art, for changing the diffusion of PDLC diffuser 100 from a maximum, to a minimum (and vice-versa) or can control a rheostat type mechanism for continuously varying the diffusion rate of PDLC diffuser 100.

Figure 8:
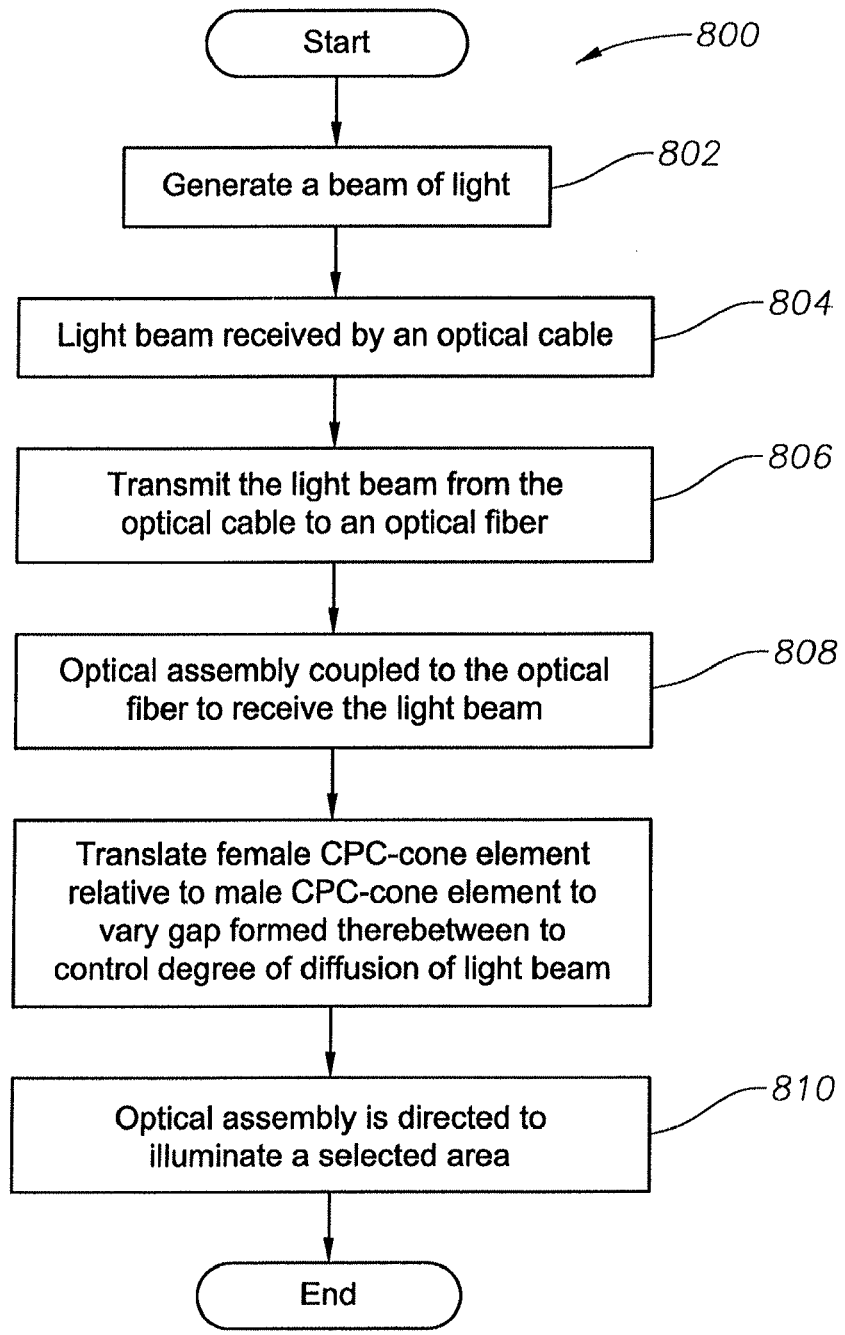
FIG. 8 is a flowchart illustrating the steps of one embodiment of the method of this invention.

FIG. 8 is a logic flow diagram illustrating a method operable to provide variable, wide-angle illumination in accordance with the teachings of this invention. Operations 800 begin with the generation of a light beam in step 802. This light beam may be generated from a light source such as light source 12 as described with reference to the prior Figures. In step 804 an optical cable receives the light beam. The light beam received by the optical cable is then transmitted to an optical fiber in step 806. In step 808 an optical assembly is coupled to the distal end of the optical fiber where the optical assembly receives the light beam. In step 810, the optical assembly is directed to illuminate a selected area in step 810. The optical assembly may spread the light beam delivered from the light source over a large area. For example, when used in ophthalmic surgery, this light beam may be delivered to the area of the retina to allow a microscopic wide-angle objective lens that permits a surgeon to see this surgical area. The angular spread of the emitted light delivered by the optical assembly may be controlled as desired in order to optimize viewing conditions within the surgical field. The optical assembly can comprise any of the embodiments described herein in accordance with the present invention.

Although the present invention has been described in detail herein with reference to the illustrated embodiments, it should be understood that the description is by way of example only and is not to be construed in a limiting sense. It is to be further understood, therefore, that numerous changes in the details of the embodiments of this invention and additional embodiments of this invention will be apparent to, and may be made by, persons of ordinary skill in the art having reference to this description. It is contemplated that all such changes and additional embodiments are within the spirit and true scope of this invention as claimed below. Thus, while the present invention has been described in particular reference to the general area of ophthalmic surgery, the teachings contained herein apply equally wherever it is desirous to provide wide-angle and variable illumination of a surgical site.

What is claimed is:

1. A variable-angle illumination surgical system comprising:
    a light source for providing a light beam;
    an optical cable, optically coupled to the light source for receiving and transmitting the light beam;
    a handpiece, operably coupled to the optical cable;
    an optical fiber, operably coupled to the handpiece, wherein the optical fiber is optically coupled to the optical cable to receive and transmit the light beam;
    an optical assembly;
    and a cannula, wherein the cannula is operably coupled to the handpiece and optical assembly for housing and directing the optical assembly to illuminate an area;
    wherein the optical assembly is optically coupled to a distal end of the optical fiber for receiving the light beam and providing the light beam to illuminate the area; wherein the optical assembly comprises a male compound parabolic concentrator (CPC) cone element nested within a female CPC-cone element, wherein the female CPC-cone element translates over the male CPC-cone element to vary an air gap formed therebetween and thereby vary the off-axis, angular spread of light emitted out of a distal end of the cannula.

2. The variable-angle illumination surgical system of claim 1, wherein the area comprises a surgical site.

3. The variable-angle illumination surgical system of claim 1, wherein the optical fiber comprises an endo-illuminator optical fiber having a 0.50 NA.

4. The variable-angle illumination surgical system of claim 1, wherein the angular spread of the light emitted by the optical assembly is determined by the proximity of the female CPC-cone element to the male CPC-cone element.

5. The variable-angle illumination surgical system of claim 1, wherein the cannula, optical assembly and the handpiece are fabricated from biocompatible materials.

6. A method for wide-angle illumination of a surgical field using a variable-angle illuminator comprising:
    generating a light beam;
    receiving the light beam with an optical cable, wherein a handpiece is operably coupled to the optical cable;
    transmitting the light beam from the optical cable to an optical fiber, wherein the handpiece is operably coupled to the optical fiber;
    optically coupling an optical assembly to a distal end of the optical fiber, wherein the optical assembly receives the light beam and comprises a male compound parabolic concentrator (CPC) cone element nested within a female CPC-cone element;
    directing the optical assembly to illuminate a selected area;
    translating the female CPC-cone element over the male CPC-cone element to vary an air gap formed between the male and female CPC-cones and thereby control the degree of diffusion of the light beam emitted out of the optical assembly.

7. The method of claim 6, wherein the directing step further comprises illuminating a surgical site.

* * * * *